United States Patent [19]

Pommrehn et al.

[11] Patent Number: 5,188,116
[45] Date of Patent: Feb. 23, 1993

[54] ELECTROCARDIOGRAPHIC METHOD AND DEVICE

[75] Inventors: Mark R. Pommrehn, Eden Prairie; James E. Brewer, Maplewood; Mark W. Kroll, Minnetonka, all of Minn.

[73] Assignee: Vital Heart Systems, Inc., Beverly, Mass.

[21] Appl. No.: 662,578

[22] Filed: Feb. 28, 1991

[51] Int. Cl.$^5$ .............................................. A61B 5/04
[52] U.S. Cl. .................................. 128/696; 128/703; 128/704
[58] Field of Search ............... 128/696, 702, 703, 704, 128/705, 715; 364/413.05, 413.06

[56] References Cited

U.S. PATENT DOCUMENTS

| | | | |
|---|---|---|---|
| 4,802,491 | 2/1907 | Cohen et al. | 128/702 |
| 4,887,609 | 12/1989 | Cole, Jr. | 128/696 |
| 5,036,857 | 8/1991 | Semmlow et al. | 128/715 |
| 5,042,497 | 8/1991 | Shapland | 128/696 |
| 5,046,504 | 9/1991 | Albert et al. | 128/696 |

Primary Examiner—William E. Kamm
Assistant Examiner—George Manuel
Attorney, Agent, or Firm—Joel D. Skinner

[57] ABSTRACT

A method and apparatus for detecting heart disease from an electrocardiogram (ECG) is disclosed. The method comprises the steps of acquiring the ECG signals, correcting for signal variability caused by breathing, and calculating the level of remaining variability due to myocardial function. The apparatus comprises a signal input system, a storage system, a microprocessor and an output system. The microprocessor has program logic for processing signal data in accordance with the above method.

12 Claims, 6 Drawing Sheets

ELECTROCARDIOGRAPHIC METHOD AND DEVICE

BACKGROUND OF THE INVENTION

This invention relates to electrocardiographic systems and methods, and particularly to a system and method for analyzing the variability in an electrocardiographic signal due to myocardial function, and which attenuates extraneous signal variability. More particularly, the system and method attenuate that portion of extraneous signal variability which is attributable to human breathing functions. The device is useful for non-invasively detecting and analyzing Coronary Artery Disease (CAD) caused by cardiac ischemia.

The resting electrocardiogram (ECG) is a standard test for heart disease. Unfortunately, its sensitivity for detecting coronary artery disease and the complications of CAD is relatively poor.

Scientific studies have shown that the variability of the electrocardiogram signal is a marker for coronary artery disease and its complications. However, to this point it has been impractical to properly measure and analyze this variability in a clinical setting because the patient's breathing causes an even larger level of variability. Breathing causes variability in the electrocardiogram signal due primarily to the changes in the geometry of the chest and tilting of the heart during lung or pulmonary function. Thus, attempts to use the variability of the electrocardiogram signal as a marker for coronary artery disease have met with limited success.

In the past, various methods and devices have been used and proposed to mitigate the effects of breathing. However, these methods and devices have generally proven to be ineffective. One known method of reduction of breathing effects utilizes a computer to repeatedly average a plurality of signal cycles to yield a composite signal which is then displayed for operator diagnosis or is further analyzed by other means. In the process of averaging, the breathing components of each signal cycle are attenuated because they are weaker than the cardiac function components. However, a problem exists in averaging techniques because they mitigate not only breathing effects, but also some low level signals and signal effects which contain relevant electrocardiographic information.

Despite the need for a system and method in the art which detects CAD and its complications by exploiting the relationship of variations in the electrocardiographic signal thereto, and which overcomes the limitations and problems of the prior art, none insofar as is known has been proposed or developed.

Accordingly, it is an object of the present invention to provide a system and method for detecting CAD and its complications in a non-invasive, stress-free manner. It is a further object of the invention to provide a system and method for quantifying and localizing cardiac ischemia.

Another object of this invention is to provide a system and method which detect and analyze variability in the electrocardiographic signal due solely to myocardial function. A further object of the invention is to provide a system and method which reduces or attenuates that portion of the variability of the electrocardiographic signal, obtained in the clinical setting, which is due to repetitive physical changes which occur in the patient's torso, particularly that which is caused by effects of breathing.

Still another object of this invention is to provide a non-invasive, stress-free electrocardiographic analysis system and method which analyzes variations in the electrocardiographic signal caused by myocardial function, without regard to breathing effects, to detect coronary artery disease with a high degree of sensitivity and specificity.

SUMMARY OF THE INVENTION

The present invention provides a method and apparatus to accurately measure the variability of the ECG signal due to cardiac function, particularly heart disease, by correcting for that portion of the signal variability which is due to breathing function.

The main feature of the electrocardiogram signal is the "R-wave" which is the generally triangular cyclical or periodic pulse which represents the electrical actuation of the ventricles of the heart. The amplitude or height of the R-wave is known to be modulated by the influence of breathing. Thus, the height of the R-wave can be used to estimate the influence of the breathing on the electrocardiogram signal. Similarly, negative peaks near the R-wave can be used to estimate the influence of breathing. These negative peaks are known as the "Q-wave" and "S-wave" which occur, respectively, just before and just after the R-wave.

The method for detecting coronary artery disease in a human being, comprises the steps of first collecting and storing a plurality of periodic electrocardiographic signals from the torso of the human body. The level of variability in the electrocardiographic signals which is due to breathing functions is then determined by (1) establishing an aggregate signal, (2) detecting and storing the peak amplitudes of the periodic electrocardiographic signals, and (3) detecting and storing the peak amplitude of the aggregate signal. The level of breathing variability is then corrected to provide a corrected electrocardiographic signal. This is accomplished by scaling the electrocardiographic signals and the template signal as a function of their respective peak amplitudes. A variance is then calculated for each corrected electrocardiographic signal. The total variability is then calculated for all corrected electrocardiographic signals. The total variability is then output, whereby the effect of variability due to breathing functions on myocardial function variability is attenuated, and whereby myocardial function variability is proportional to the degree of coronary artery disease.

The system for detecting coronary artery disease in a human being, comprises means for receiving a plurality of periodic electrocardiographic signals from the body, means for storing the signals, and a microprocessor. The microprocessor has means for determining the level of variability in the electrocardiographic signals which is due to breathing function. The determination means first calculates an aggregate signal with respect to the plurality of signals, and second detects and stores the peak amplitudes of the plurality of signals and the aggregate signal. The microprocessor also has means for correcting the level of breathing variability. The correction means provides a corrected electrocardiographic signal by scaling the plurality of signals and the average signal as a function of their respective peak amplitudes. The microprocessor further has means for calculating a variance for the corrected signal and means for calculating the total variance of the plurality of signals. Finally, the system comprises means for outputting the total variance, whereby the effect of variability due to breathing function on myocardial function variability is attenuated.

A principle teaching of this invention is a method and means for removing the variability in the electrocardiogram signal due to breathing, during testing or monitoring in a clinical setting, so that the variability attributable to myocardial function can be accurately measured. These and other benefits of this invention will become clear from the following description by reference to the drawings.

DESCRIPTION OF THE PREFERRED EMBODIMENT

Figure 1:
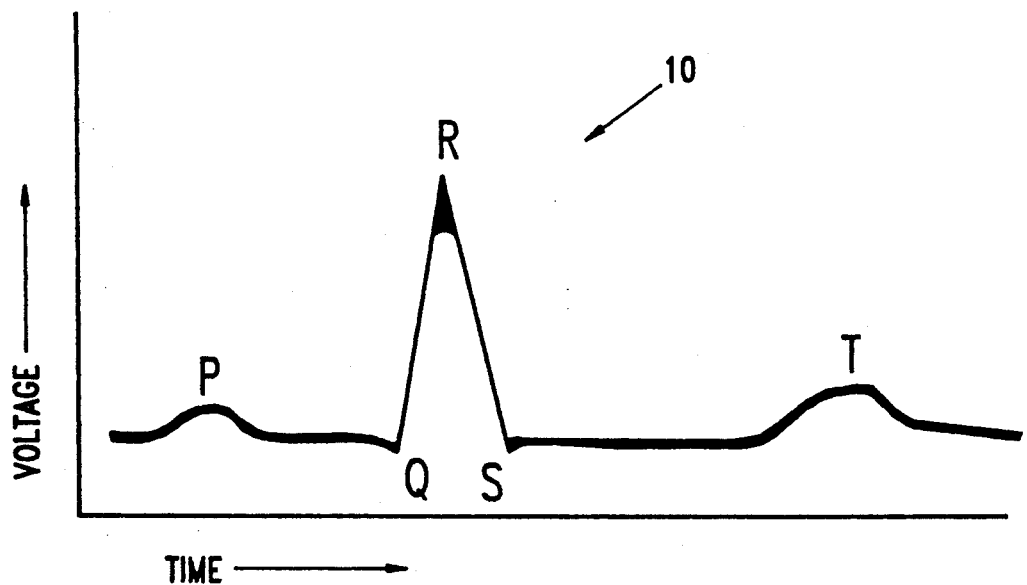
FIG. 1 shows an idealized human periodic electrocardiographic signal record or trace for a single heartbeat.
Figure 2:
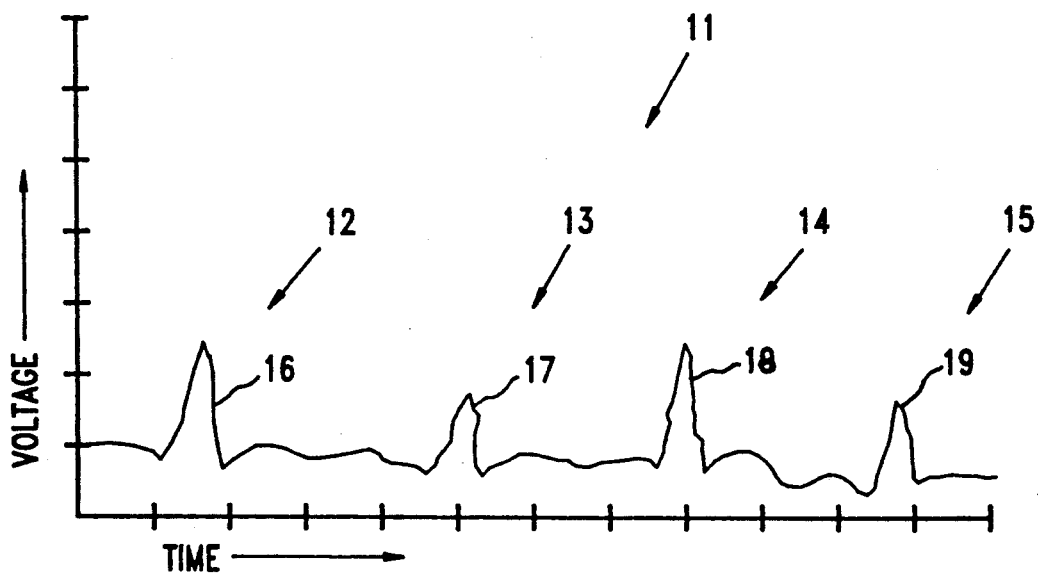
FIG. 2 shows a standard human electrocardiographic signal covering several heartbeats and showing the variability caused by breathing.
Figure 3:
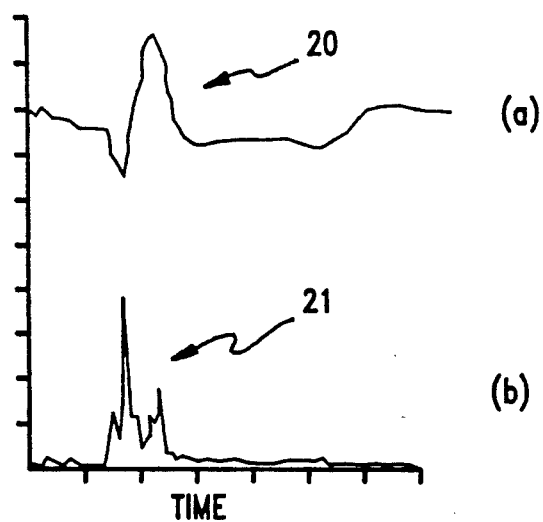
FIG. 3 shows an exemplary human electrocardiographic variability waveform (b) aligned below its corresponding aggregate waveform (a)

The method and system of the present invention may be better understood by reference to FIGS. 1-3, which show electrocardiographic signals. FIG. 1 shows an idealized electrocardiogram signal 10 record for a single signal cycle or period which represents the electrical events occurring during a single heartbeat. Beginning at the left, the first feature is the P-wave. Following the P-wave are the Q-wave, the main feature of highest amplitude is the R-wave, and then the S-wave. The largely triangular portion is often referred to as the QRS complex. The final feature of the heartbeat signal is the T-wave.

FIG. 2 shows an electrocardiogram signal 11 covering several heartbeats 12-15 and showing the variability caused by breathing. The first beat R-wave 16 has a relatively large height or amplitude while the second beat R-wave 17 has a lower height. The third beat R-wave 18 has a large height again while that of the fourth beat R-wave 19 is relatively lower in amplitude. The present invention utilizes the amplitude modulation of the ECG signal cycles as an estimate of the influence of breathing activity on variation in the ECG signal. As previously discussed, variability in the ECG signal due to myocardial function is highly relevant to the diagnosis of CAD, and, therefore, the removal of the effects of breathing on ECG signal variability is the focus of the method and system of the present invention.

Averaging the cyclical signals yields an average or aggregate signal in which the predominant electrical constituents attenuate variability due to breathing effects. The heartbeat electrocardiogram signals are aligned or synchronized, each aligned heartbeat signal being referred to as $x(t)$. These raw beats ("n" in number) are then averaged to produce a single average beat referred to as $m(t)$, in accordance with:

$$m(t) = \frac{1}{n} \sum_{j=1}^{n} x_j(t)$$

The average or template beat $m(t)$ 20, as shown for example in FIG. 3(a), has essentially no breathing influence remaining.

Amplitude characteristics such as peak measurements are utilized as an estimate of breathing influence on the ECG signals. The peaks are measured for each beat $x(t)$. First, the positive peak of each heartbeat $x(t)$ is measured and referred to as $V_{pp}$. For heartbeat number "j", the positive peak is labeled $V_{pp}(j)$. The positive peak of the mean or aggregate beat is labeled $V_{pp}(m)$.

The negative peaks may be found in either the Q-wave or the S-wave of each cycle. Whichever is more negative, is utilized as the negative peak and labeled $V_{nn}(j)$ and $V_{nn}(m)$ for the raw beats and the mean beat, respectively.

An adjustment or scaling between the template and raw beats affects a matching which corrects for the influence of breathing on the raw signals. In one version of the scaling, the mean beat is repeatedly scaled up or down to match the peaks of each raw beat $x(t)$. The scaled beats are referred to as $\beta(t)$ and the number "j" scaled beat is labeled $\beta_j(t)$. The positive portions of aggregate signal $m(t)$ are scaled so that the positive peaks $V_{pp}$ match as described below:

$$t \quad m(t) \geq 0: \quad \beta_j(t) = \frac{V_{pp}(j)}{V_{pp}(m)} m(t)$$

The negative portions of aggregate signal $m(t)$ are scaled so that the negative peaks $V_{nn}$ match as described below:

$$t \quad m(t) < 0: \quad \beta_j(t) = \frac{V_{nn}(j)}{V_{nn}(m)} m(t)$$

The scaled beats $\beta_j(t)$ may be utilized to calculate a pseudo-variance 21 or temporal heterogeneity waveform, as shown, for example, in FIG. 3(b), as follows:

$$\lambda(t) = \frac{1}{n} \sum_{j=1}^{n} [x_j(t) - \beta_j(t)]^2$$

The $\lambda(t)$ is then integrated across the time span defined as $[t_o, t_k]$, where $t_o$ represents the first time position for the aggregate beat $m(t)$, and where $t_k$ represents the last time position for the aggregate beat $m(t)$. To perform the integration, the first step is to compute the sum of the differences between each time value of the temporal heterogeneity waveform and the waveform baseline, $\lambda B$:

$$\sum_{t=t_o}^{t_k} (\lambda(t) - \lambda_B).$$

The second step is to normalize the sum by:

$$T^*[V_{pp}(m) - V_{nn}(m)]^2$$

to compensate the waveform measurement for the lead to lead variability of R-wave amplitude.

Therefore, a non-breathing variability (TV) index for each lead analyzed is:

$$TV = \frac{\sum_{t=t_o}^{t_k} \lambda(t) - \lambda_B}{T^*[V_{pp}(M) - V_{nn}(M)]^2}$$

Then, all leads or signals are summed to yield the total variability:

$$TTV = \sum_{i=1}^{n} T_i,$$

where
  i=each lead or electrocardiographic signal.

Scaling may alternatively be accomplished wherein the raw beats x(t) are scaled to match the peaks of the mean beats m(t) instead of the mean beat m(t) being scaled to match the peaks of the raw beats x(t).

In yet another alternative version of the scaling, the aggregate beat is repeatedly scaled up or down to match the peak-to-peak voltage amplitude of each raw beat.

Each voltage sample of the aggregate beat is scaled so the peak-to-peak voltages match as described below:

$$t: \beta_j = \frac{V_{pp}(j) - V_{nn}(j)}{V_{pp}(m) - V_{nn}(m)}$$

The scaled beats are then used to calculate the pseudo-variance as previously described.

Figure 4:
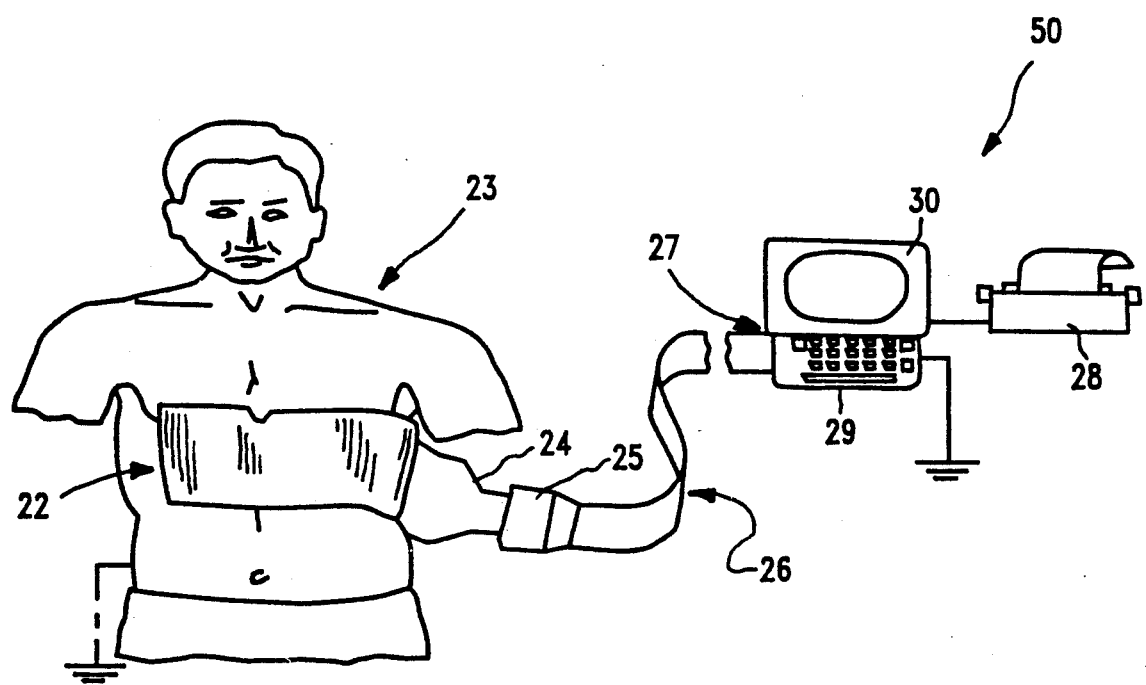
FIG. 4 is a frontal view of a human being showing typical connections of an electrode apparatus to the torso, and further showing the operator interface components of the system of the present invention.

Referring to FIG. 4, the system 50 of the present invention for removal of breathing variability and calculating the variability due to electrocardiographic activity is shown. A flexible electrode belt 22 is positioned in an operative position on the torso of a human patient 23. The electrode belt 22 is used to receive an electric current or voltage from the body of the patient. A plurality of discrete electrodes, each having a separate lead, as known in the art, are also useable with the system of the present invention. The terminal end 24 of belt 22 is connectible to a connector 25 of a cable set 26 which is connected to the operator interface components 27 of the system 50. Additionally as shown, the device 27 may be communicatively linked to a printer 28 to receive hard copy. The connector 25 serves as an interface between the belt device 22 and the standard ribbon or other type of cable 26, and also may house current limiting devices 49 to protect the patient 23 from shock.

Figure 5:
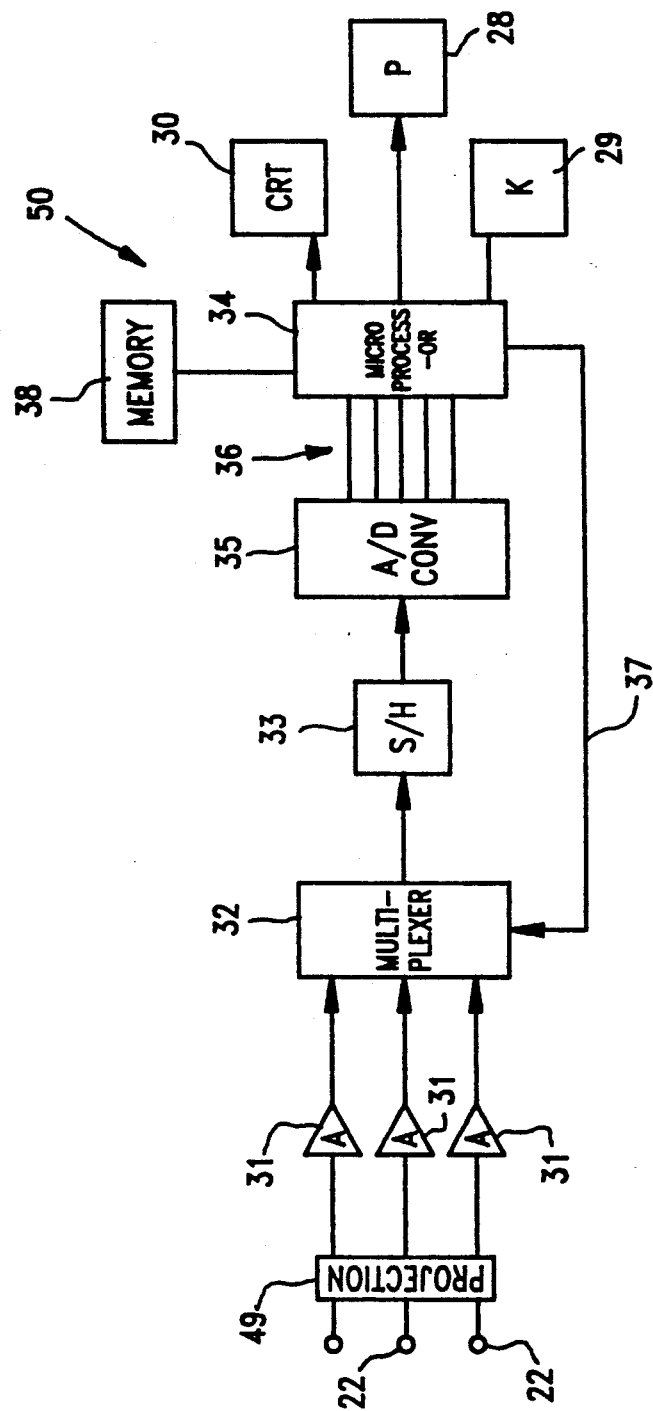
FIG. 5 is a schematic diagram showing the basic functional components of the system of the present invention.

Referring to FIG. 5, the system 50 of the present invention acquires and analyzes ECG signals from the torso of the patient 23 via the patient interface components shown in FIG. 4 and previously discussed. Basically, the system 50 acquires the ECG signals from the electrodes 22, amplifies the signals and digitizes them. The digitized signals are then transmitted to a microprocessor 34 for analysis and subsequent output via a cathode ray tube display (CRT) 30, or in hard copy form on the printer 28. The operator controls the process sequence from signal acquisition to analysis and output via a keyboard 29, and further has feedback from the system 50 via the CRT 30.

ECG signals from the various electrodes 22 are transmitted to a set of amplifiers 31, one of which is connected in-line with each electrode 22. A current limiting circuit 49 is shown to be placed in-line with the electrodes 22. The amplified signals are then input to a multiplexer 32 which selects predetermined signals to be input to and sampled by a sample-and-hold circuit 33. The multiplexer 32 is shown to be under the program control of the microprocessor 34. Alternatively, it may be connected to a separate logic sequencing circuit. The signals transmitted from the human body 23 to this point in the circuit are analog signals. The sample-and-hold circuit 33 outputs the analog signals to a 16 bit analog to digital converter 35 which digitizes the signals, preferably at a rate of approximately 1,536,000 bits/sec. The digital signals are then output to the microprocessor 34. The analog to digital converter 35 is connected to the microprocessor 34, via a data bus 36, either by a direct electrical connection or an optical coupling via an optical isolator. Additionally, the control line 37 between the microprocessor 34 and the multiplexer 32 may be either electrical or opto-electrical.

The microprocessor 34 controls both data acquisition and analysis in the system 50. The microprocessor 34 is communicatively connected via a system bus to a memory 38, including read only memory (ROM), random access memory (RAM), and disk storage. The design and interconnection of these components is generally known in the art. As also shown, the microprocessor 34 is communicatively connected to the display 30, preferably via a graphics controller; to the keyboard 29, preferably via a keyboard interface; and to the printer 28, preferably via a parallel printer interface. The graphics controller is controlled via the microprocessor 34, under program control thereof. The keyboard 29 and printer 28 interface directly with their respective controllers.

The microprocessor 34 executes the process steps of the invention, which are discussed in detail below, via program logic or control instructions (software) which are stored in the ROM or alternatively a disk storage. The RAM basically provides a buffer memory for signal data.

Figure 6:
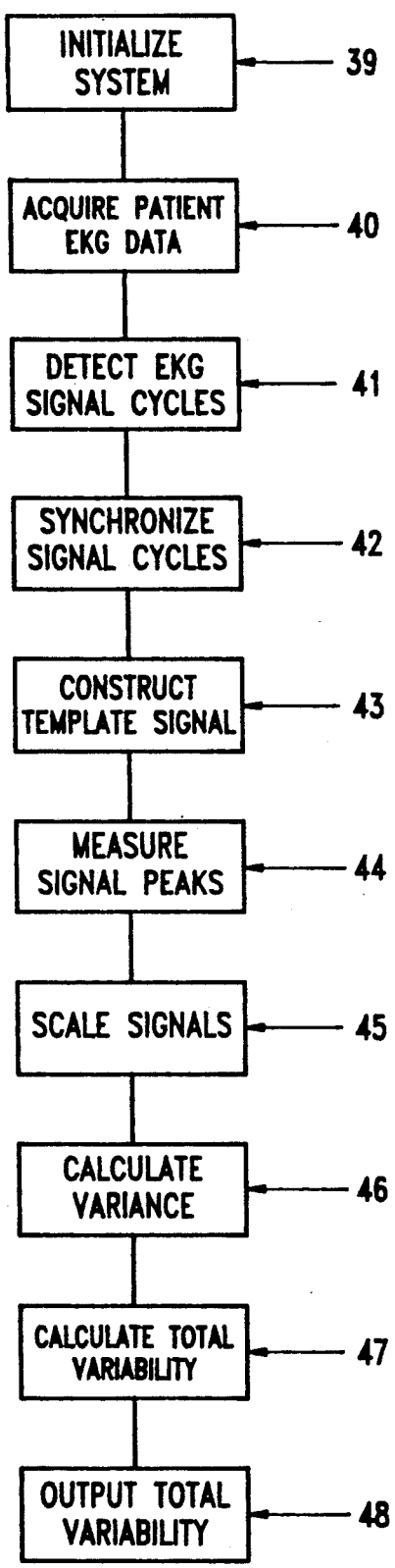
FIG. 6 is a flow chart of the basic process of the present invention for determining the electrocardiographic variability of a human body, which process is implemented by the system of the present invention.

After activation and initialization 39 of the system 50, the microprocessor 34 performs the sequence of basic process steps shown in FIG. 6. First, the system acquires a plurality of ECG signals 40 for approximately 15 minutes via its input device 22. Next, the system detects the individual raw beats 41 in the signal via a standard robust QRS complex detection means. This is accomplished via QRS complex detection techniques, as known in the art.

The system 50 then aligns the raw beats 42 and constructs an average or aggregate beat 43. This is accomplished via computer averaging techniques as known in the art. Preferably alignment 42 is accomplished via a terrain biased, dynamic multiple threshold synchronization method and means described below.

The system 50 then measures the peak amplitudes of the raw ECG periodic signals and of the average or template signals 44. Preferably, both positive and negative peaks of the respective raw and average signals are detected and stored as discussed in further detail below.

The system 50 utilizes the stored peak amplitude data to then scale the raw and average signals 45, whereby their respective signal constituents match. Scaling of the signals provides a corrected signal which is free of breathing variability. Particular scaling methods are further discussed below.

The system 50 then processes the corrected signals for variability 46. First, variance is calculated in accordance with:

$$\lambda(t) = \frac{1}{n} \sum_{j=1}^{n} [x_j(t) - \beta_j(t)]^2,$$

where
$\lambda(t)$ = variance,
n = total number of signals,
j = specific beat counter,
$X_j(t)$ = the $j^{th}$ beat signal, and
$\beta(t)$ = scaled beat.

The resultant signal 21 is shown, for example in FIG. 3(b). Secondly, $\lambda(t)$, the temporal heterogeneity waveform 21, is integrated to yield a non-breathing variability index in accordance with:

$$\text{Variability} = \frac{1}{T} \int_{\text{heartbeat}} \lambda(t) dt,$$

where
T = total length of the averaged beat in time,
$\lambda(t)$ = beat to beat variance, and
t = integral time scale.

Finally, the system 50 outputs the variability 48 via the various output devices discussed above.

Figure 7:
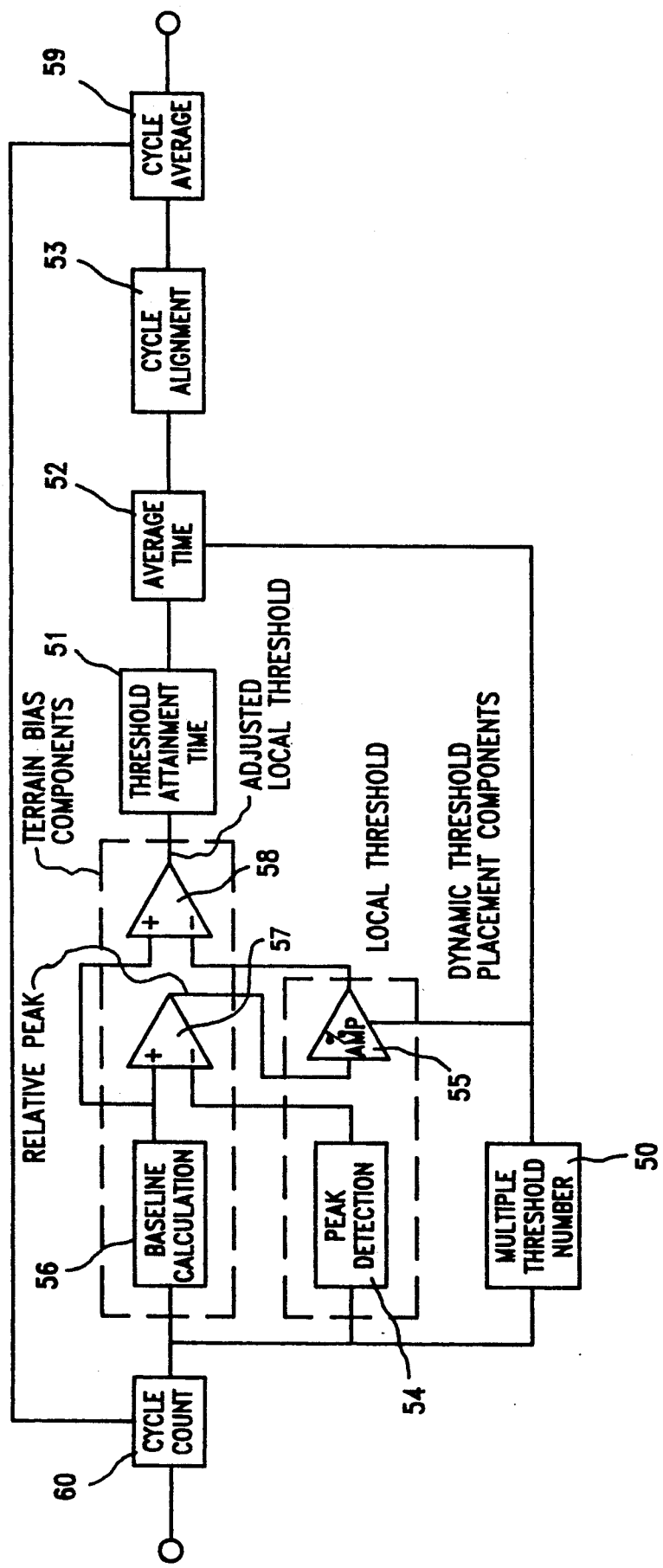
FIG. 7 is a data flow map showing an embodiment of the process and system for synchronizing ECG signal cycles and calculating an aggregate signal.

Referring to FIG. 7, the microprocessor 34 preferably synchronizes the periodic electrocardiographic signals via a Terrain Biased Dynamic Multiple Threshold Synchronization system as taught in U.S. Pat. No. 4,769,760, which is hereby incorporated by reference. This establishes an accurate time reference for synchronizing the input electrocardiographic signals, and which reduces the deleterious effects of signal noise in establishing a precise time coordinate for synchronizing the signals for subsequent averaging and other processing.

The alignment process steps first involve determining a predetermined number of threshold points 50. The multiple threshold points are discrete voltage levels set for each individual signal cycle. Next the actual baseline of each cycle is calculated 56, preferably over an isoelectric region. The peak voltage of each cycle is then determined 54. Next, the actual baseline is subtracted from the peak voltage 57 yielding a relative peak voltage.

The multiple threshold points are then positioned as percentages of the relative peak voltage 55 yielding set of local threshold points for each cycle. Finally, the position of each local threshold point is adjusted by adding the actual baseline of the cycle 58 to yield a set of adjusted local voltage threshold points.

Next, the time is calculated at which each adjusted local threshold point is attained by the cycle being analyzed 51. Each observed time coordinate pertaining to the particular cycle is then summed and divided by the total number of threshold attainment times 52 to yield a mean threshold attainment time or alignment time. Preferably, each observed sample threshold time is assigned a weighing factor prior to averaging to yield weighted mean threshold times. This accomplished by utilizing a digital filter of a type known in the art to generate weighting criteria in conjunction with mean threshold time determination.

The weighted mean threshold times are utilized as a common reference point from which to align each cycle 53. Each cycle is aligned with respect to the weighted mean threshold time, thus shifting all signal data of each cycle. This alignment establishes a relative time scale for representing the voltage samples of the individual cycles.

Corresponding voltage data points on each cycle are next averaged 59 in the microprocessor 34 to yield the composite or aggregate signal. For each relative time position, the voltage samples from each cycle are summed and divided by the total number of cycles sampled 60 to derive a mean voltage. The microprocessor 34 repeats this process for each relative time interval.

Figure 8:
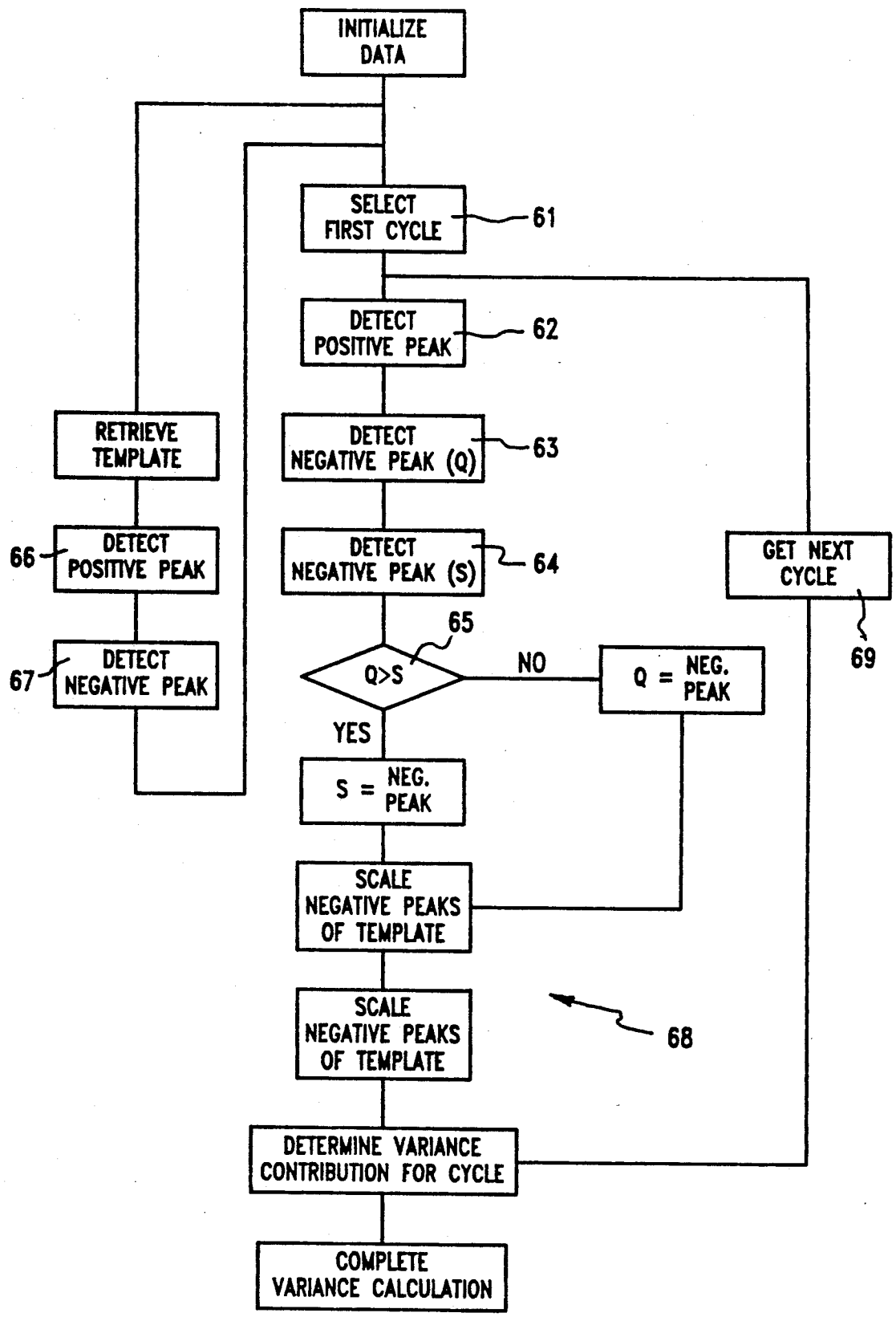
FIG. 8 is a flow chart showing a process for the determination of cycle peaks, and for scaling an aggregate signal to match raw ECG signal cycles, and which is implemented by the system of the invention.

Referring to FIG. 8, the peak detection steps include retrieving both the raw ECG signals and the template signal from data storage. With respect to the raw ECG signals, a first period or cycle is selected 61 including the entire QRS complex. The positive peak amplitude of the R-wave is detected 62. The negative peaks of the Q-wave 63 and the S-wave 64 are then detected and it is determined which has a greater negative value 65. Additionally, positive 66 and negative 67 peak amplitude detection is accomplished with respect to the aggregate signal.

Still referring to FIG. 8, the raw ECG and template peak data is shown to be utilized in the scaling process. As shown, the average signal is scaled either up or down with respect to both positive and negative peak amplitudes 68 to match the raw ECG signal as previously described. The next succeeding raw ECG signals then undergo peak detection and use in scaling the average signal 69. Upon the processing of all ECG signals, the scaled signals are processed for variability as discussed above.

It will be apparent to those skilled in the art that an alternative scaling process consistent with the teachings of the invention, and which may be implemented by the system, involves scaling the raw ECG signals cycles to match the average signal.

As many changes are possible to the embodiments of this invention utilizing the teachings thereof, the descriptions above, and the accompanying drawings should be interpreted in the illustrative and not the limited sense.

That which is claimed is:

1. A method of analyzing electrocardiographic activity for detecting coronary artery disease in a human being, comprising the steps of:
   a) collecting and storing electrocardiographic signals from the body, each said electrocardiographic signal having a plurality of cycles;
   b) establishing an aggregate cycle for each said electrocardiographic signal;
   c) for each said electrocardiographic signal, determining the level of variability in said electrocardiographic signal which is due to breathing by:
      i) detecting and storing amplitude characteristics of said signal cycles;
      (ii) detecting and storing amplitude characteristics of said signal aggregate cycle;

iii) adjusting said signal cycles and said aggregate cycles so that their respective said amplitude characteristics match;

iv) calculating a variance by: i') comparing each said adjusted signal cycle to said adjusted aggregate cycle, and ii') combining said comparisons;

d) calculating the total variability for all electrocardiographic signals based on said calculated variances;

e) outputting said calculated total variability, whereby the effect of variability due to breathing on myocardial variability detection is attenuated; and f) quantifying the magnitude of coronary artery disease, whereby an increase in said total variability is proportional to the magnitude of coronary artery disease.

2. The method of analyzing electrocardiographic activity of claim 1, wherein said step of establishing said aggregate cycle comprises the steps of synchronizing said electrocardiographic signal cycles and averaging said synchronized cycles.

3. The method of analyzing electrocardiographic activity of claim 2, wherein said step of synchronizing said electrocardiographic signal cycles comprises the steps of:

a) selecting a plurality of discrete threshold voltage points, said threshold points generally corresponding to a predetermined range of voltages of said signal cycles;

b) determining threshold times at which each said threshold voltage point is attained by each said signal cycle; and c) calculating an average threshold time for each said signal cycle; and d) synchronizing said signal cycles based on said average threshold times, said synchronizing further including the steps of establishing a relative time scale for representing the voltage variable of each said signal cycle based on said average threshold times and aligning said relative time scales with respect to their average threshold times.

4. The method of analyzing electrocardiographic activity of claim 1, wherein said amplitude characteristics are points of highest and lowest amplitudes on each said electrocardiographic signal cycle and said aggregate cycle.

5. The method of analyzing electrocardiographic activity of claim 4, wherein said adjusting step comprises the steps of repeatedly scaling said aggregate cycle in amplitude to match each said electrocardiographic signal cycle.

6. The method of analyzing electrocardiographic activity of claim 1, wherein said amplitude characteristics are the algebraic differences between points of highest and lowest amplitude on each said electrocardiographic signal cycle and said aggregate cycle.

7. The method of analyzing electrocardiographic activity of claim 6, wherein said adjusting step comprises the steps of repeatedly scaling said aggregate cycle in amplitude to match each electrocardiographic signal cycle.

8. The method of analyzing electrocardiographic activity of claim 1, wherein said adjusting step comprises the steps of scaling said periodic electrocardiographic signal cycles in amplitude to match said aggregate cycle.

9. A system for analyzing electrocardiographic activity for detecting coronary artery disease in a human being, comprising:

a) means for receiving a plurality of periodic electrocardiographic signals from the body, each said electrocardiographic signal having a plurality of cycles;

b) means for storing said signals;

c) a microprocessor having i) means for calculating an aggregate cycle for each said electrocardiographic signal, ii) means for detecting and storing amplitude characteristics of said plurality of signal cycles and said aggregate cycles, iii) means for adjusting said plurality of signal cycles and their respective said aggregate cycles as a function of their respective amplitude characteristics to provide a plurality of adjusted signals, iv) means for calculating a variance for each said adjusted signal, whereby the level of variability in each said electrocardiographic signal which is due to breathing is determined, said adjustment means comparing each said signal cycle to its respective said aggregate cycle and combining said comparisons, and v) means for calculating the total variance of the plurality of said adjusted signals based on said calculated variances;

d) means for outputting said calculated total variance, whereby the effect of variability due to breathing on myocardial variability detection is attenuated; and e) means for quantifying the magnitude of coronary artery disease, whereby an increase in said total variability is proportional to the magnitude of coronary artery disease.

10. The system for analyzing electrocardiographic activity of claim 9, wherein said means for receiving includes at least one electrode for placement in direct contact with the body, at least one means, connected to said electrode, to amplify signals output by said electrode, means to multiplex said amplified signal, and means to digitize said multiplexed signal.

11. The system for analyzing electrocardiographic activity of claim 9, wherein said microprocessor includes means to receive signal data from said detection means in serial format, program logic instructions for processing said signal data, and means for controlling the input and output of data from said means for detecting signals and said means for outputting total variance.

12. The system for analyzing electrocardiographic activity of claim 9, wherein said means for calculating an aggregate cycle comprises:

a) means for synchronizing a predetermined number of input signal cycles including:

i) means for determining an actual baseline voltage of each said signal cycle;

ii) means for determining a peak amplitude of each said signal cycle;

iii) means for subtracting said actual baseline voltage from said peak amplitude to yield a relative peak amplitude for each said signal cycle;

iv) means for calculating a plurality of threshold voltage points, said points corresponding to a percentage of said relative peak amplitude for each said signal cycle;

v) means for adding said actual baseline voltage to each said threshold voltage point to yield adjusted threshold voltage points for each said signal cycle; and vi) means for determining threshold times at which said adjusted threshold voltage points are attained by each said signal cycle; and b) means for averaging said synchronized signal cycles.

* * * * *